(12) United States Patent
Ha et al.

(10) Patent No.: US 10,537,476 B2
(45) Date of Patent: *Jan. 21, 2020

(54) OPHTHALMIC TREATMENT APPARATUS AND BEAM CONTROL METHOD THEREFOR

(71) Applicant: Lutronic Vision Inc, Burlington, MA (US)

(72) Inventors: Tae Ho Ha, Goyang (KR); Cheol San An, Goyang (KR)

(73) Assignee: Lutronic Vision Inc, Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/139,998

(22) Filed: Sep. 24, 2018

(65) Prior Publication Data
US 2019/0021903 A1  Jan. 24, 2019

Related U.S. Application Data

(63) Continuation of application No. 14/414,696, filed as application No. PCT/KR2013/006331 on Jul. 15, 2013, now Pat. No. 10,080,683.

(30) Foreign Application Priority Data

Jul. 13, 2012 (KR) .................. 10-2012-0076779

(51) Int. Cl.
*A61F 9/008* (2006.01)
*A61F 9/007* (2006.01)

(52) U.S. Cl.
CPC ............ *A61F 9/008* (2013.01); *A61F 9/0079* (2013.01); *A61F 9/0084* (2013.01); *A61F 9/00814* (2013.01); *A61F 9/00823* (2013.01); *A61F 9/00825* (2013.01); *A61F 2009/00844* (2013.01)

(58) Field of Classification Search
CPC .................................. A61F 9/008–2009/00897
USPC ............................................... 606/4–6, 10–12
See application file for complete search history.

(56) References Cited

U.S. PATENT DOCUMENTS 9,033,963 B2 * 5/2015 Vera ..................... A61F 9/00821
606/4
2003/0073983 A1 4/2003 Bille
2006/0111697 A1 5/2006 Brinkmann et al.
(Continued)

OTHER PUBLICATIONS

International Search Report for PCT/KR2013/006331, dated Oct. 25, 2013.

*Primary Examiner* — Gary Jackson
*Assistant Examiner* — Jonathan Kuo (57) ABSTRACT

The present invention relates to an ophthalmic treatment apparatus and to a beam control method therefor. The ophthalmic treatment apparatus according to the present invention comprises: a beam generating unit for generating beams having different pulse energies; a bubble sensing unit for sensing whether or not bubbles have been generated, as well as the amount of generated bubbles, on the basis of the pulse energy of the beam generated by the beam generating unit and radiated onto the treatment region of an eyeball; and a control unit for controlling the operation of the beam generating unit such that the pulse energy of the beam generated by the beam generating unit can be adjusted in accordance with the signal from the bubble sensing unit.

14 Claims, 10 Drawing Sheets

(56) References Cited

U.S. PATENT DOCUMENTS

2010/0021983 A1 1/2010 Vogel
2012/0259321 A1* 10/2012 Vera .................... A61F 9/00821
606/6

* cited by examiner

OPHTHALMIC TREATMENT APPARATUS AND BEAM CONTROL METHOD THEREFOR

CROSS-REFERENCE TO RELATED APPLICATION

This application is a continuation of U.S. patent application Ser. No. 14/414,696, filed Jan. 13, 2015, now U.S. Pat. No. 10,080,683 issued Sep. 25, 2018, which is a U.S. National Stage Application of PCT/KR2013/006331 filed Jul. 15, 2013, which claims priority to Korean Patent Application 10-2012-0076779 filed Jul. 13, 2012, which are hereby incorporated by reference in their entirety.

BACKGROUND OF THE INVENTION

Field of the Invention

The present invention relates to an ophthalmic treatment apparatus and a method of controlling, by the ophthalmic treatment apparatus, beams and, more particularly, to an ophthalmic treatment apparatus for measuring pulse energy of a beam for treatment that is radiated to the treatment region of an eyeball and radiating a beam for treatment that is suitable for the treatment region of the eyeball and a method of controlling, by the ophthalmic treatment apparatus, beams.

Related Art

An ophthalmic treatment apparatus is used for the purpose of treating ocular diseases, such as glaucoma, a cataract, and macular degeneration. In this case, glaucoma of the ocular diseases is a disease attributable to an increase in the intraocular pressure of an eyeball, and a cataract is a disease attributable to the whitening phenomenon of the crystalline lens. Furthermore, macular degeneration is an ocular disease generated in the retina.

In order to treat various ocular diseases, the ophthalmic treatment apparatus radiates beams for treatment which have wavelength bands having different pulse energy. For example, the ophthalmic treatment apparatus may radiate a beam for treatment having pulse energy of a wavelength band of 1064 nm depending on the tissue of an ocular disease.

Meanwhile, a conventional ophthalmic treatment apparatus has been disclosed in "Korean Patent Application Publication No. 2011-0063100" entitled "Apparatus for the Treatment of Ocular Diseases and Apparatus for the Diagnosis of Ocular Diseases." The apparatus for the treatment of ocular diseases and apparatus for the diagnosis of ocular diseases, that is, the prior art document, discloses a technical characteristic in which an ocular disease is treated by radiating a femtosecond laser having a controlled focus to the vitreous humour within an eyeball so that a pressure wave attributable to laser-caused ionization and laser-caused absorption within the vitreous humour of a focal zone is generated.

However, the technical characteristic disclosed in the conventional prior art document is for treating an ocular disease by radiating the femtosecond laser to the vitreous humour of an eyeball and is problematic in that treatment efficiency may be deteriorated because treatment is performed without testing a laser having pulse energy suitable for different ocular tissue.

SUMMARY OF THE INVENTION

An object of the present invention is to provide an ophthalmic treatment apparatus capable of testing the suitability of pulse energy of a beam for treatment on ocular tissue so that a beam for treatment having pulse energy corresponding to different ocular tissue can be radiated and of performing treatment and a method of controlling, by the ophthalmic treatment apparatus, beams.

According to the present invention, means for solving the object is accomplished by an ophthalmic treatment apparatus, including a beam generation unit which generates beams having different types of pulse energy, a bubble detection unit which detects whether a bubble is generated or the amount of bubbles generated according to the pulse energy of the beams generated by the beam generation unit and radiated to the treatment region of an eyeball, and a control unit which controls the operation of the beam generation unit based on a signal from the bubble detection unit so that the pulse energy of the beams generated by the beam generation unit is controlled.

In this case, the beams generated by the beam generation unit may include a beam for test which is radiated so that the bubble detection unit detects whether a bubble is generated and the amount of bubbles generated and a beam for treatment which corresponds to pulse energy of the beam for test when the bubble detection unit detects whether a bubble is generated and the amount of bubbles generated and which is radiated in order to treat the treatment region of the eyeball.

Preferably, a region to which the beam for test is radiated may be a test region, that is, one region of the treatment region of the eyeball.

The control unit preferably controls the operation of the beam generation unit so that the pulse energy of the beam for test generated by the beam generation unit is sequentially increased until the bubble detection unit detects the generation of a bubble.

Furthermore, the ophthalmic treatment apparatus may further include a memory unit which stores information about each of types of pulse energy that are sequentially increased until a bubble is detected by the bubble detection unit.

Preferably, when the beam for test is radiated to a test region, that is, the other region of the treatment region of the eyeball, the control unit may control the operation of the beam generation unit so that the radiation is started from pulse energy that belongs to information about types of pulse energy of beams radiated to a previous test region and that is greater than minimum pulse energy and is smaller than pulse energy when a bubble is detected by the bubble detection unit, wherein the information about the types of pulse energy of the beams is stored in the memory unit.

More preferably, the control unit may control the operation of the beam generation unit so that the beam for treatment is radiated with corresponding pulse energy when the bubble detection unit detects the generation of a bubble.

Furthermore, the control unit may sequentially increase the pulse energy of the beam for test until the bubble detection unit detects the generation of a bubble, may maintain corresponding pulse energy by which a bubble is generated, and may control the operation of the beam generation unit until the bubble detection unit detects a predetermined amount of bubbles.

Meanwhile, according to the present invention, means for solving the object is accomplished by a method of controlling, by an ophthalmic treatment apparatus, beams, wherein the ophthalmic treatment apparatus includes a beam generation unit generating beams having different types of pulse energy, and the method includes steps of (a) generating the beams radiated to a test region, that is, one region of the treatment region of an eyeball, and radiating the beams to the test region, (b) detecting whether a bubble is generated in the test region according to the radiation of the beams, and (c) controlling the operation of the beam generation unit based on whether a bubble is generated so that the pulse energy of the beams are controlled.

In this case, the method may further include a step of (d) controlling the operation of the beam generation unit so that a beam having corresponding pulse energy when the generation of a bubble is detected at the step (c) is radiated to treat the treatment region of the eyeball.

The beams generated by the beam generation unit may include a beam for test radiated to the test region and a beam for treatment which has pulse energy corresponding to pulse energy of the beam for test at the step (d) and which is radiated to the treatment region of the eyeball.

Furthermore, the step (c) may include a step of sequentially increasing the pulse energy of the beam for test until the generation of a bubble is detected in the test region.

Furthermore, the ophthalmic treatment apparatus includes a memory unit which stores information about each of types of pulse energy. The method may include a step of controlling the operation of the beam generation unit so that the beam for test is radiated with pulse energy that belongs to the information about each of the types of pulse energy stored in the memory unit and that is one step lower than information about pulse energy when a bubble is generated when the beam for test is radiated to a test region that is the other region of the treatment region of the eyeball.

The step (b) may include a step of detecting the generation of a bubble and the amount of bubbles generated.

Furthermore, the step (c) may include a step of controlling the operation of the beam generation unit until a predetermined amount of bubbles is detected by radiating corresponding pulse energy when the bubble is generated, wherein the corresponding pulse energy is stored in the memory unit.

The details of other embodiments are included in the detailed description and the drawings.

The ophthalmic treatment apparatus and the method of controlling, by the ophthalmic treatment apparatus, beams according to the present invention are advantageous in that information about pulse energy of a beam for treatment that corresponds to tissue of a treatment region can be obtained because a beam for test is radiated to the treatment region of an eyeball before the beam for treatment is radiated to the treatment region of the eyeball and thus the treatment efficiency and safety of the treatment region can be secured.

DESCRIPTION OF EXEMPLARY EMBODIMENTS

Hereinafter, an ophthalmic treatment apparatus and a method of controlling, by the ophthalmic treatment apparatus, beams in accordance with embodiments of the present invention are described in detail with reference to the accompanying drawings.

Prior to a description, it is to be noted that the elements of ophthalmic treatment apparatuses in accordance with first and second embodiments of the present invention are the same and thus the same elements are assigned the same reference numerals.

Furthermore, the ophthalmic treatment apparatus to be described below in accordance with embodiments of the present invention is illustrated as treating a lesion of the retina, but may be applied to other ocular diseases in addition to a lesion of the retina.

In particular, a beam generation unit hereinafter is illustrated as generating two beams: a beam for test and a beam for treatment. It is to be noted that the two beams are not individually generated, but the beam for test is a beam whose pulse energy is controlled until a signal is detected by a bubble detection unit and the beam for treatment is a beam radiated for treatment with pulse energy corresponding to pulse energy of a corresponding test beam until a signal is detected by the bubble detection unit.

Figure 1:
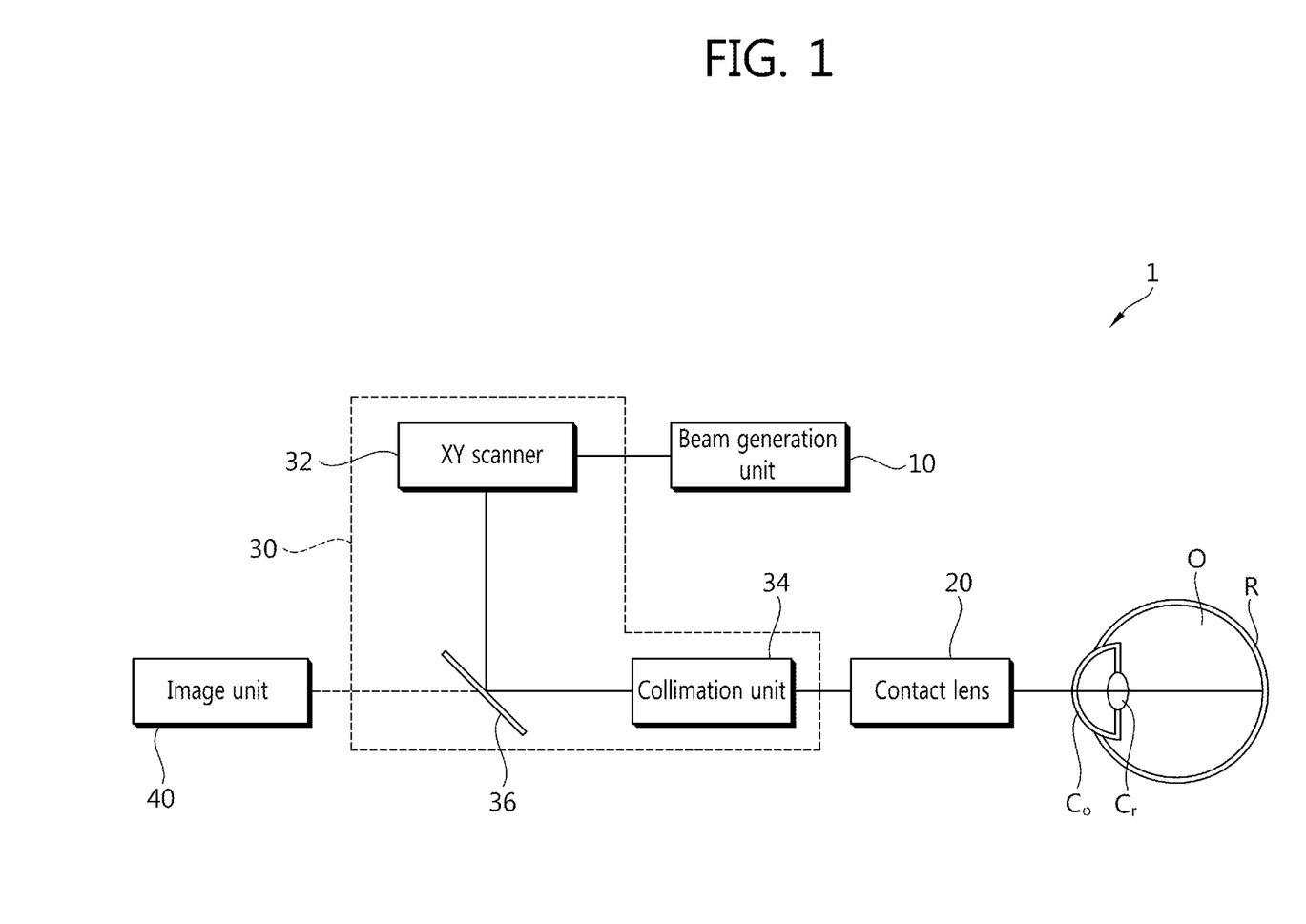
FIG. 1 is a schematic configuration diagram of an ophthalmic treatment apparatus in accordance with embodiments of the present invention.
Figure 2:
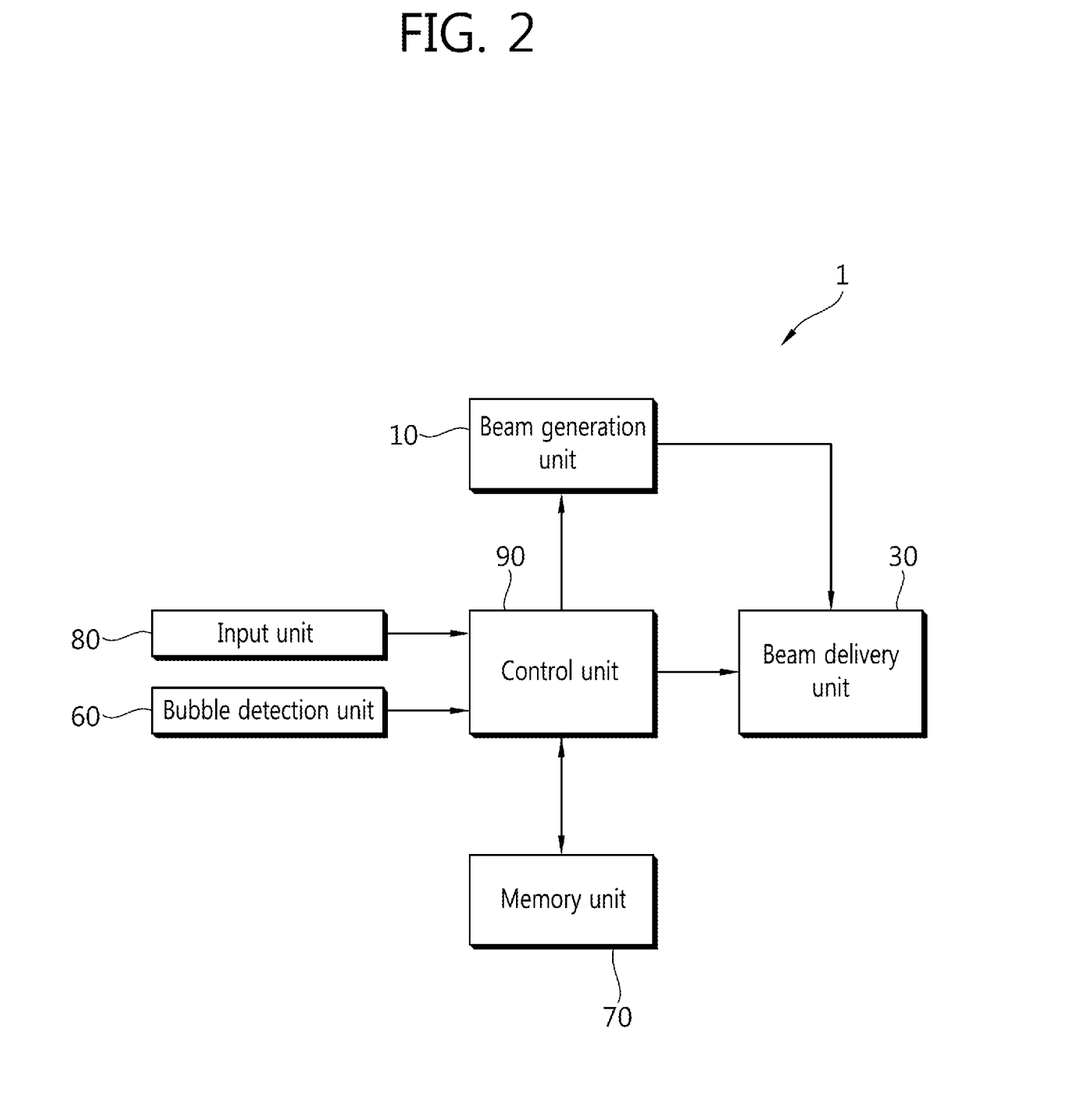
FIG. 2 is a control block diagram of the ophthalmic treatment apparatus in accordance with embodiments of the present invention.
Figure 3:
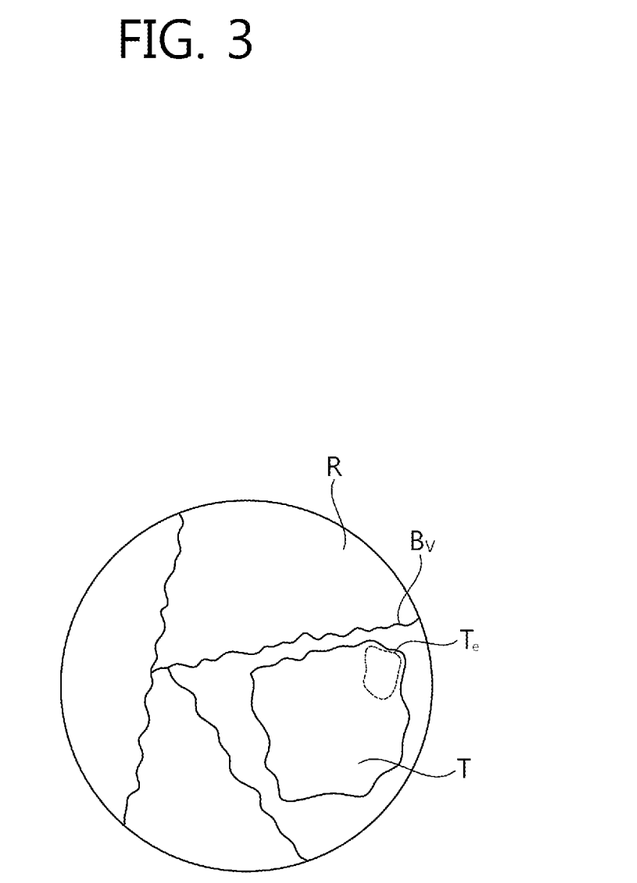
FIG. 3 is a schematic configuration diagram of a treatment region to which a beam for treatment is radiated by the ophthalmic treatment apparatus in accordance with embodiments of the present invention and a test region to which a beam for test is radiated.

FIG. 1 is a schematic configuration diagram of an ophthalmic treatment apparatus in accordance with embodiments of the present invention, FIG. 2 is a control block diagram of the ophthalmic treatment apparatus in accordance with embodiments of the present invention, and FIG. 3 is a schematic configuration diagram of a treatment region to which a beam for treatment is radiated by the ophthalmic treatment apparatus in accordance with embodiments of the present invention and a test region to which a beam for test is radiated.

As illustrated in FIGS. 1 to 3, the ophthalmic treatment apparatus 1 in accordance with embodiments of the present invention includes a beam generation unit 10, a contact lens 20, a beam delivery unit 30, an image unit 40, a bubble detection unit 60, a memory unit 70, an input unit 80, and a control unit 90. In this case, the contact lens 20 of the ophthalmic treatment apparatus 1 in accordance with embodiments of the present invention may be omitted depending on the location of a lesion region.

The beam generation unit 10 generates a beam for treatment for treating a lesion generated in the retina R of an eyeball O. Furthermore, the beam generation unit 10 generates a beam for test that is used to generate a beam for treatment of pulse energy suitable for tissue of the treatment region T of the eyeball O. The test beam generated by the beam generation unit 10 may have various wavelength bands according to pulse energy. In this case, the beam for treatment and the beam for test generated by the beam generation unit 10 include lasers. In response to a control signal from the control unit 90, the beam generation unit 10 generates test beams having different types of pulse energy and also generates beams for treatment having corresponding pulse energy after a test of tissue of the eyeball O is terminated using the beam for test.

The contact lens 20 comes in contact with the cornea Co of the eyeball O and guides the beam for treatment or test beam, generated by the beam generation unit 10, to the retina R through the crystalline lens Cr of the eyeball O.

The beam delivery unit 30 includes an XY scanner 32, a collimation unit 34, and a beam splitter 36. The beam delivery unit 30 is disposed between the beam generation unit 10 and the contact lens 20. The beam delivery unit 30 guides the beam for treatment, generated by the beam generation unit 10 and incident thereon, to the treatment region T of the eyeball O. In this case, the beam generation unit 10 and the beam delivery unit 30 are driven based on an operation signal received from the input unit 80.

Assuming that the optical axial line of the beam for treatment radiated to the eyeball O is a Z axis, the XY scanner 32 functions to determine the focal location of the beam for treatment on an XY plane, that is, a plane perpendicular to the Z axis. For example, the XY scanner 32 includes at least two reflection mirrors not illustrated in the present invention and controls the focal location of the beam for treatment along the X axial line and the Y axial line.

The collimation unit 34 is disposed between the XY scanner 32 and the contact lens 20. The collimation unit 34 collimates the beam for treatment, provided by the XY scanner 32, to the contact lens 20. An object lens including a combination of a plurality of lenses is used as the collimation unit 34. The beam splitter 36 is disposed between the XY scanner 32 and the collimation unit 34. The beam splitter 36 guides the beam for treatment from the XY scanner 32 to the collimation unit 34.

The image unit 40 forms an image by photographing the eyeball O. The image unit 40 may consist of various known combinations, such as Optical Coherence Tomography (OCT) and a digital camera. The retina R, a blood vessel BV, the treatment region T, and a test section Te illustrated in FIG. 3 are photographed by the image unit 40, being forming into an image. As described above, the image of the eyeball O formed by the image unit 40 can improve treatment efficiency of an operator.

The bubble detection unit 60 detects whether a bubble according to the beam for test generated by the beam generation unit 10 and radiated to the treatment region T of the eyeball O has been generated and the amount of bubbles generated according to the beam for test. The bubble detection unit 60 detects whether a bubble has been generated in the ophthalmic treatment apparatus 1 in accordance with a first embodiment of the present invention. In contrast, the bubble detection unit 60 detects whether a bubble has been generated and the amount of bubbles generated in the ophthalmic treatment apparatus 1 in accordance with a second embodiment of the present invention. In this case, the bubble detection unit 60 may use an optical detection method. For example, the bubble detection unit 60 may be configured to detect whether a bubble has been generated and the amount of bubbles generated using the degree that light is scattered by bubbles. In this case, the bubble detection unit may be configured using various known methods.

The memory unit 70 stores a detection signal detected by the bubble detection unit 60. The memory unit 70 stores information about each of types of pulse energy that are sequentially increased until a bubble is detected by the bubble detection unit 60 in the ophthalmic treatment apparatus 1 in accordance with the first embodiment of the present invention. Furthermore, the memory unit 70 stores information about pulse energy when a predetermined amount of bubbles is detected along with information about each of types of pulse energy that are sequentially increased until a bubble is detected by the bubble detection unit 60. In this case, the information about pulse energy when the predetermined amount of bubbles is detected, which is stored in the memory unit 70, includes information about the time when the predetermined amount of bubbles is detected along with information when a bubble is generated.

The input unit 80 is provided to apply operation signals to the beam generation unit 10, the beam delivery unit 30, and the image unit 40. When applying an operation signal to the beam generation unit 10, the input unit 80 separately applies an operation signal for generating beams for treatment and an operation signal for generating beams for test.

The control unit 90 generates control signals for controlling the operations of the beam generation unit 10, the beam delivery unit 30, and the image unit 40 based on input from the input unit 80. In some embodiments, the control unit radiates a beam for test and a beam for treatment that generates a bubble, while controlling the operation of the beam generation unit 10 so that pulse energy of a beam for test generated by the beam generation unit 10 is sequentially increased until the bubble detection unit 60 detects the generation of the bubble.

Meanwhile, if a beam for test is radiated in an adjacent location again after a beam for treatment is radiated to a specific location, the size of the beam for test may be determined by taking the previously radiated beam for treatment into consideration. For example, it is assumed that test beams having types of pulse energy P1, P2, and P3 have been sequentially radiated to a location X1 (P1<P2<P3<P4), a bubble has been generated in the beam having the pulse energy of P4, and the P4 has been determined to be a beam for treatment. In this case, it may be expected that a bubble may occur even at a location X2 adjacent to the location X1 if a beam having pulse energy similar to the P4 is radiated. Accordingly, if a beam for test is to be radiated to the location X2, pulse energy is not sequentially increased from the pulse energy P1 as in the location X1, but the beam for test may be radiated so that the pulse energy is sequentially increased from the pulse energy P2 or P3. In this case, there is an advantage in that the time taken for treatment can be reduced. Accordingly, the first pulse energy of a beam for test radiated at a subsequent location may be controlled so that it has a value greater than that of a beam for test radiated at a previous location. Alternatively, the first pulse energy of a beam for test radiated at a subsequent location may be controlled so that it is sequentially increased with energy of 70~90% of a beam for treatment radiated at a previous location.

Meanwhile, after a test of tissue of the eyeball O using a beam for test is terminated, the control unit 90 controls the operation of the beam generation unit 10 so that a beam for treatment is radiated with corresponding pulse energy when the bubble detection unit 60 detects the generation of a bubble.

Furthermore, in some embodiments of the present invention, the control unit 90 sequentially increases pulse energy of a beam for test until the bubble detection unit 60 detects the generation of a bubble, maintains corresponding pulse energy by which a bubble has been generated, and controls the operation of the beam generation unit 10 until the bubble detection unit 60 detects a predetermined amount of bubbles. A radiation time may be taken into consideration along with pulse energy of a beam for treatment that is radiated to tissue of the eyeball O because the control unit 90 controls the operation of the beam generation unit 10 so that a beam for test is generated until a predetermined amount of bubbles is detected as described above.

<First Embodiment>

Figure 4:
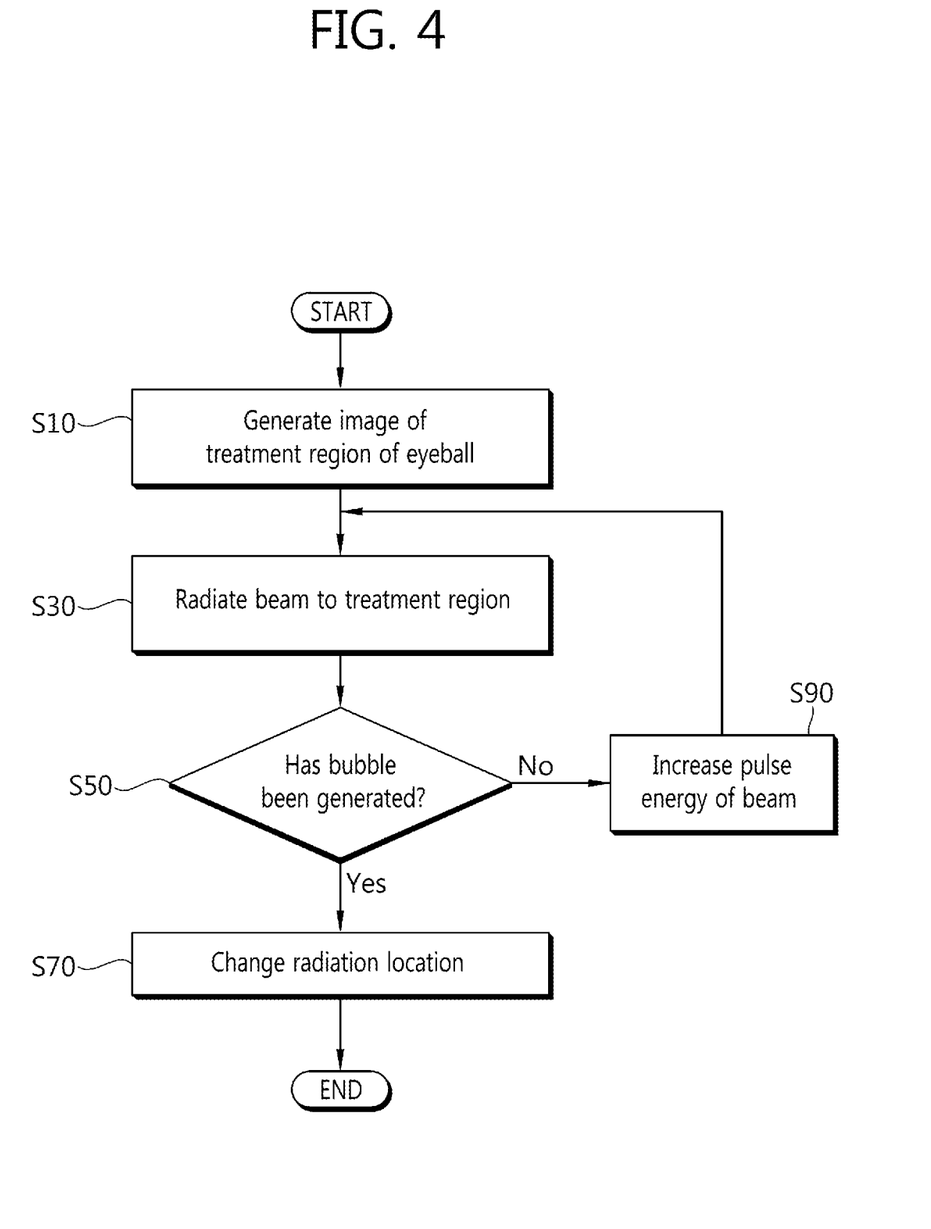
FIG. 4 is a control flowchart illustrating the ophthalmic treatment apparatus in accordance with a first embodiment of the present invention.
Figure 5:
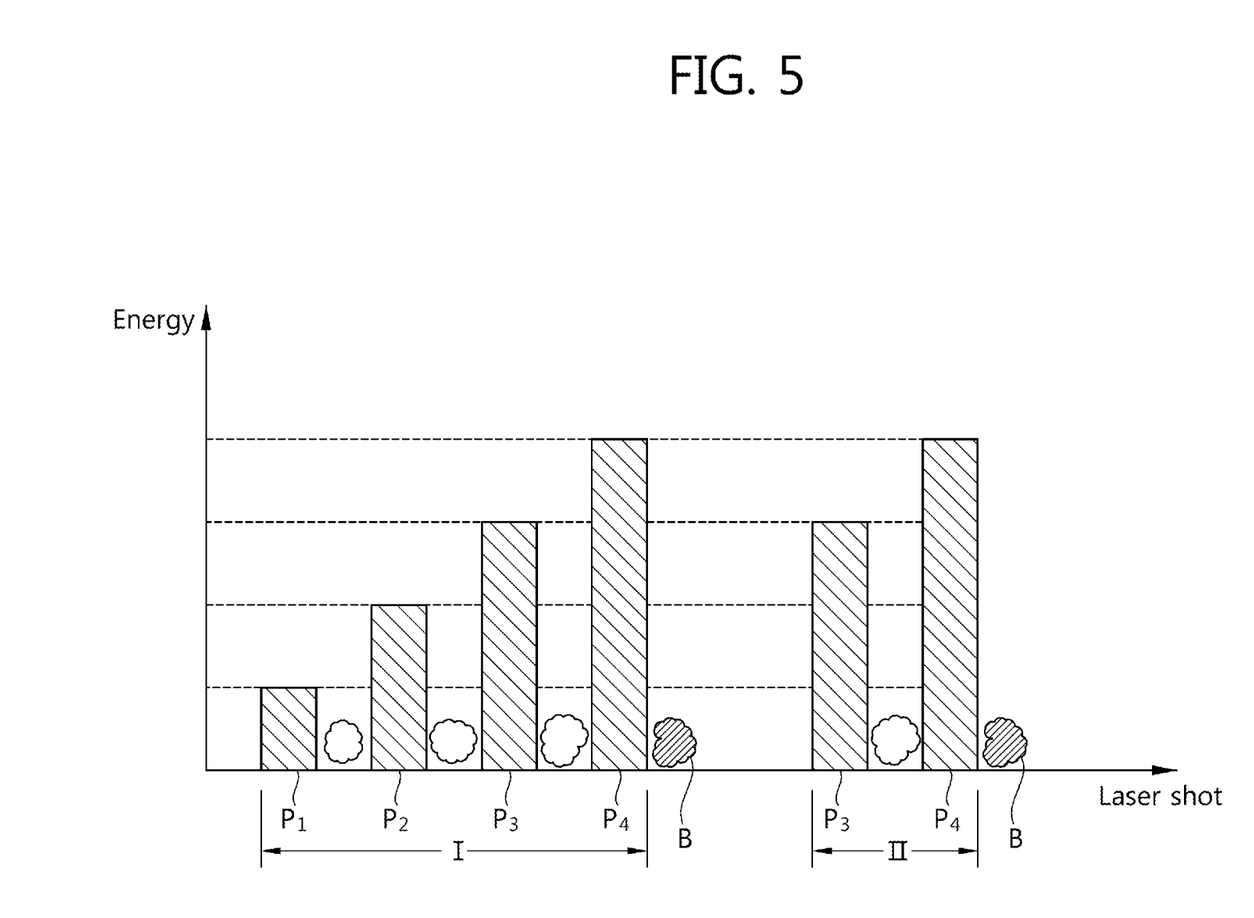
FIG. 5 is a graph illustrating the amounts of energy of beams radiated in accordance with a first embodiment of the present invention.

FIG. 4 is a control flowchart illustrating the ophthalmic treatment apparatus in accordance with the first embodiment of the present invention, and FIG. 5 is a graph illustrating the amounts of energy of beams radiated in accordance with the first embodiment of the present invention.

A method of controlling, by the ophthalmic treatment apparatus 1, beams in accordance with the first embodiment of the present invention is described below.

As illustrated in FIG. 4, first, an image is formed by photographing the treatment region T of the eyeball O (S10).

Next, a beam is radiated to a first treatment location of the treatment region T (S30). Next, whether a bubble B has been generated is detected using the bubble detection unit 60 (S50). If a bubble is determined to have not been generated at step S50 of detecting a bubble, pulse energy of the beam is controlled so that it is increased (S90). Next, a beam is radiated to the same treatment location (S30), and whether a bubble has been generated is determined (S50).

Thereafter, if it is detected that the bubble B has been generated at step of detecting a bubble, information about the pulse energy of the corresponding beam is stored in the memory unit. Furthermore, it is determined that treatment has been performed on a corresponding treatment location. The radiation location is moved by controlling the beam delivery unit so that the beam is radiated to another treatment location (S70), and treatment is performed.

FIG. 5 illustrates the sizes of pulse energy of beams radiated as described above. As illustrated in FIG. 5, a beam P1 that is first radiated at a first treatment location I of the treatment region T is configured to have low pulse energy in order to prevent unexpected damage to the retina. Furthermore, beams P2, P3, and P4 are radiated while sequentially increasing the pulse energy until a bubble is generated. After all the beams are radiated, whether a bubble has been generated is determined. Furthermore, if the generation of a bubble is detected, treatment at the first treatment location I is determined to have been completed. The beam is moved to a second treatment location II.

Furthermore, as in the previous treatment location, even at the second treatment location II, treatment may be performed by radiating beams using a method of sequentially increasing energy of the beam.

In this case, at the first treatment location, the beams have been radiated in such a way as to sequentially increase energy from a beam having the lowest energy for safety reason. At the second treatment location, it may be expected that treatment will be performed using a beam having an energy amount similar to that at the first treatment location. Accordingly, the amount of energy of the beam P4 by which the bubble has been generated at the first treatment location is stored in the memory unit. Energy of the first beam radiated at the second treatment location II may be controlled so that it is smaller than that of the beam P4 by which the bubble has been generated at the first treatment location I, but is greater than that of the first beam P1 at the first treatment location I. In the present embodiment, as illustrated in FIG. 5, at the second treatment location, a beam may be radiated so that the amount of energy is sequentially increased from P3. In this case, when a bubble is generated by a second beam, treatment may be completed.

<Second Embodiment>

Figure 6:
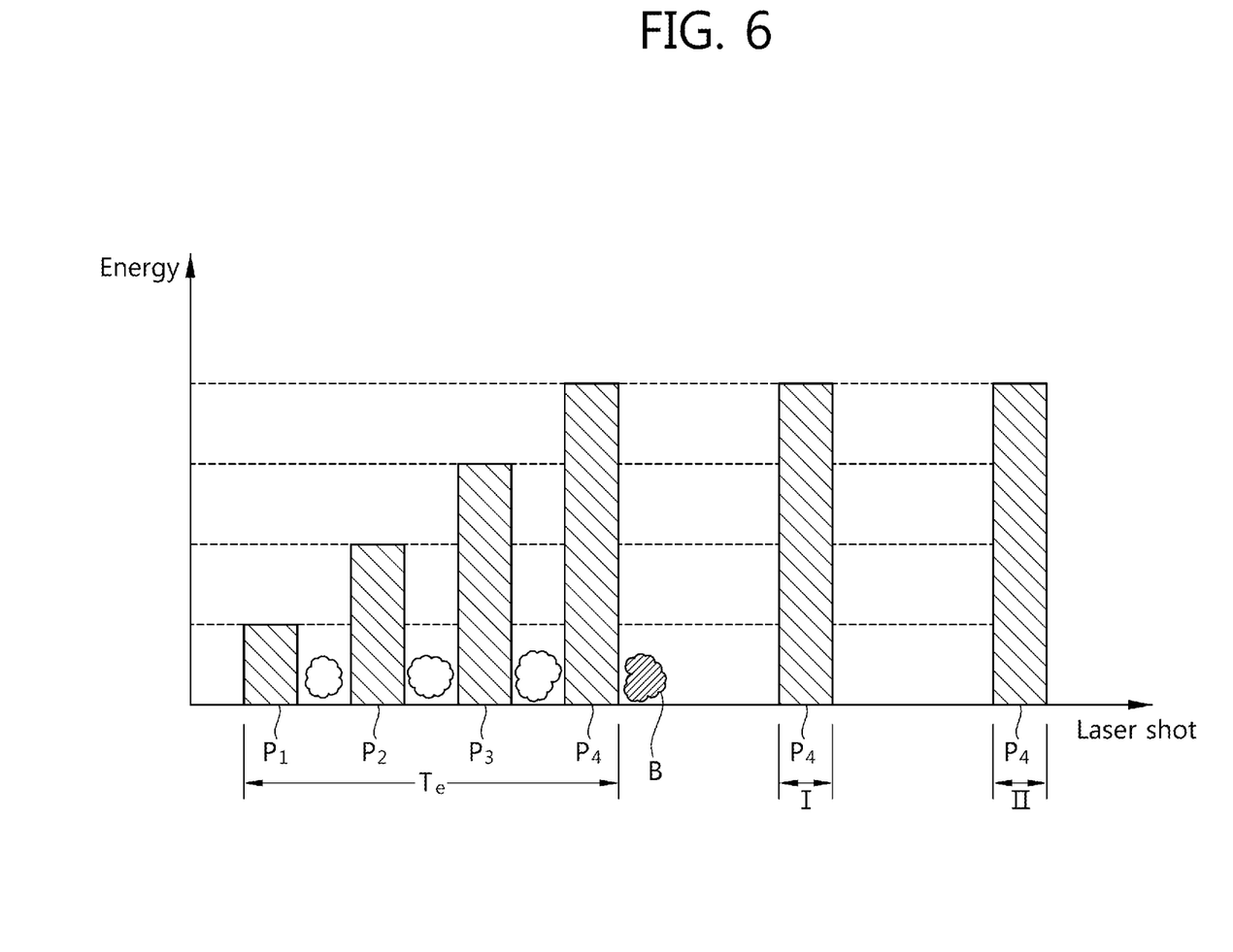
FIG. 6 is a graph illustrating the amounts of energy of beams radiated in accordance with a second embodiment.

FIG. 6 is a graph illustrating the amounts of energy of beams radiated in accordance with a second embodiment. In the first embodiment, whether a bubble is generated is detected while sequentially increasing the amount of a beam according to each treatment location, and whether treatment has been completed has been determined. In contrast, in the present embodiment, on the assumption that the amounts of beams for treatment in a treatment region are similar, some region of the treatment region T may be set as a test section Te, the amount of energy of a beam for treatment in the corresponding test section Te may be determined, and treatment may be performed by radiating beams having the same energy to the remaining treatment locations of the treatment region T based on the determined amount.

As illustrated in FIG. 6, first, beams are radiated to the test region so that energy is sequentially increased from a beam of low energy. In this case, if the generation of a bubble at P4 is detected, pulse energy of the beam for treatment is determined to correspond to pulse energy of P4 based on the detection, and treatment may be performed in such a way as to radiate a beam, having energy equal to that of P4, to the remaining treatment regions.

In FIG. 6, it has been determined that the amount of the last beam P4 by which the bubble has been generated in the test region may generate a beam even at another treatment location and thus a beam having the same amount has been radiated. In this case, energy of beams previously radiated several times in the test region may remain in treatment locations to some extent without being discharged. Accordingly, the amount of a beam for treatment may be determined to be greater than that of P4 at a specific ratio, and treatment for the remaining treatment locations may be performed.

<Third Embodiment>

Figure 7:
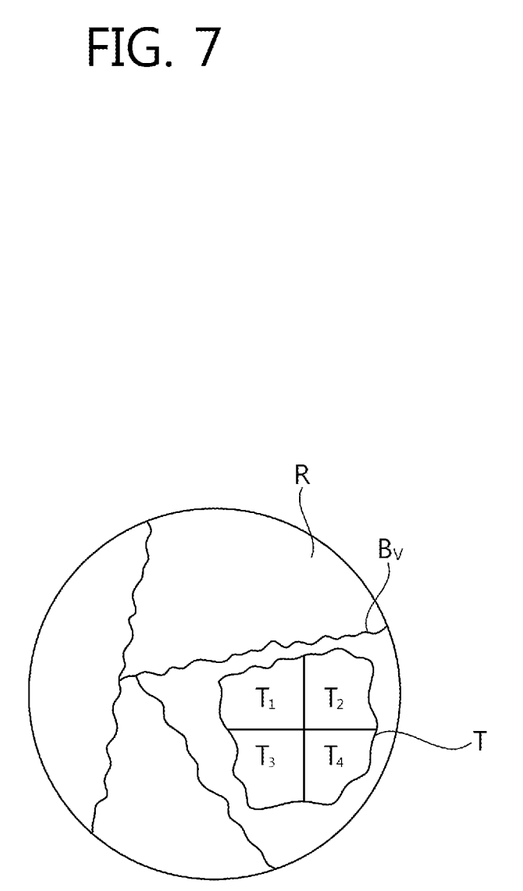
FIG. 7 is a diagram illustrating that a treatment region has been partitioned according to a third embodiment.
Figure 8:
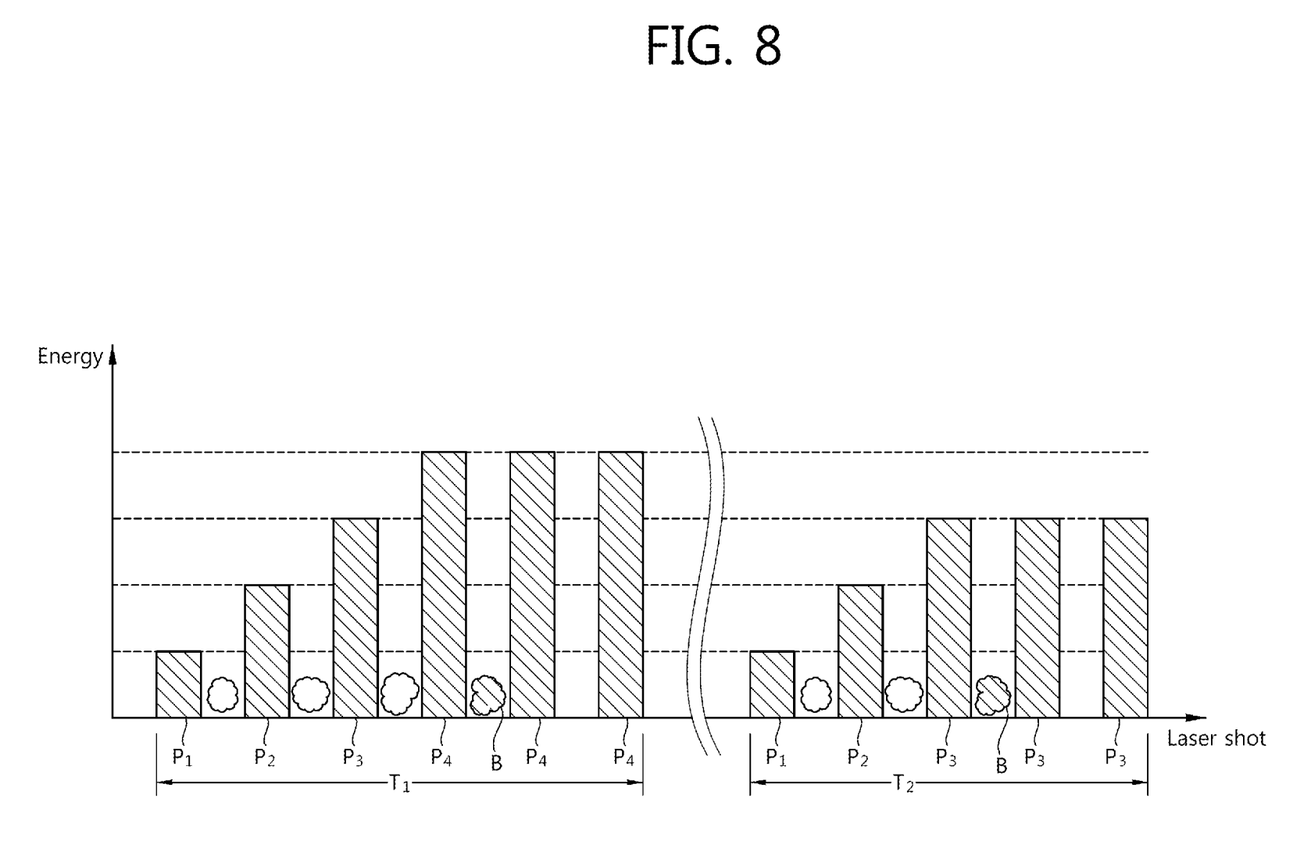
FIG. 8 is a graph illustrating the amounts of energy of beams radiated according to a third embodiment.

FIG. 7 is a diagram illustrating that a treatment region has been partitioned according to a third embodiment, and FIG. 8 is a graph illustrating the amounts of energy of beams radiated according to a third embodiment.

In the second embodiment, the entire treatment region has been treated using the amount of a beam for treatment determined in a single test region. In the present embodiment, however, a treatment region may be partitioned into a plurality of sections T1, T2, T3, and T4 having a similar tissue characteristic, a test region may be set in each section, the amount of a beam for treatment may be determined in each section, and treatment may be performed using the amount of a corresponding beam for treatment for only a corresponding section.

As illustrated in FIG. 8, first, after a test region is determined in the section T1, the amount of energy of a beam by which a bubble is generated is determined while sequentially increasing energy from a beam having a small amount in the corresponding test region. In this case, if a bubble is generated at P4, treatment for the remaining treatment locations of the section T1 may be performed using a beam having pulse energy at P4. Thereafter, likewise, even in the section T2, the amount of energy of a beam for treatment is determined while sequentially increasing energy of a beam in the test region of the section T2. In this case, if a bubble is generated at P3, treatment for the remaining treatment locations of the section T2 may be performed using a beam having pulse energy at P3.

Furthermore, although not illustrated in FIG. 8, treatment for the sections T3 and T4 may be performed using a method similar to that of the sections T1 and T2.

<Fourth Embodiment>

Figure 9:
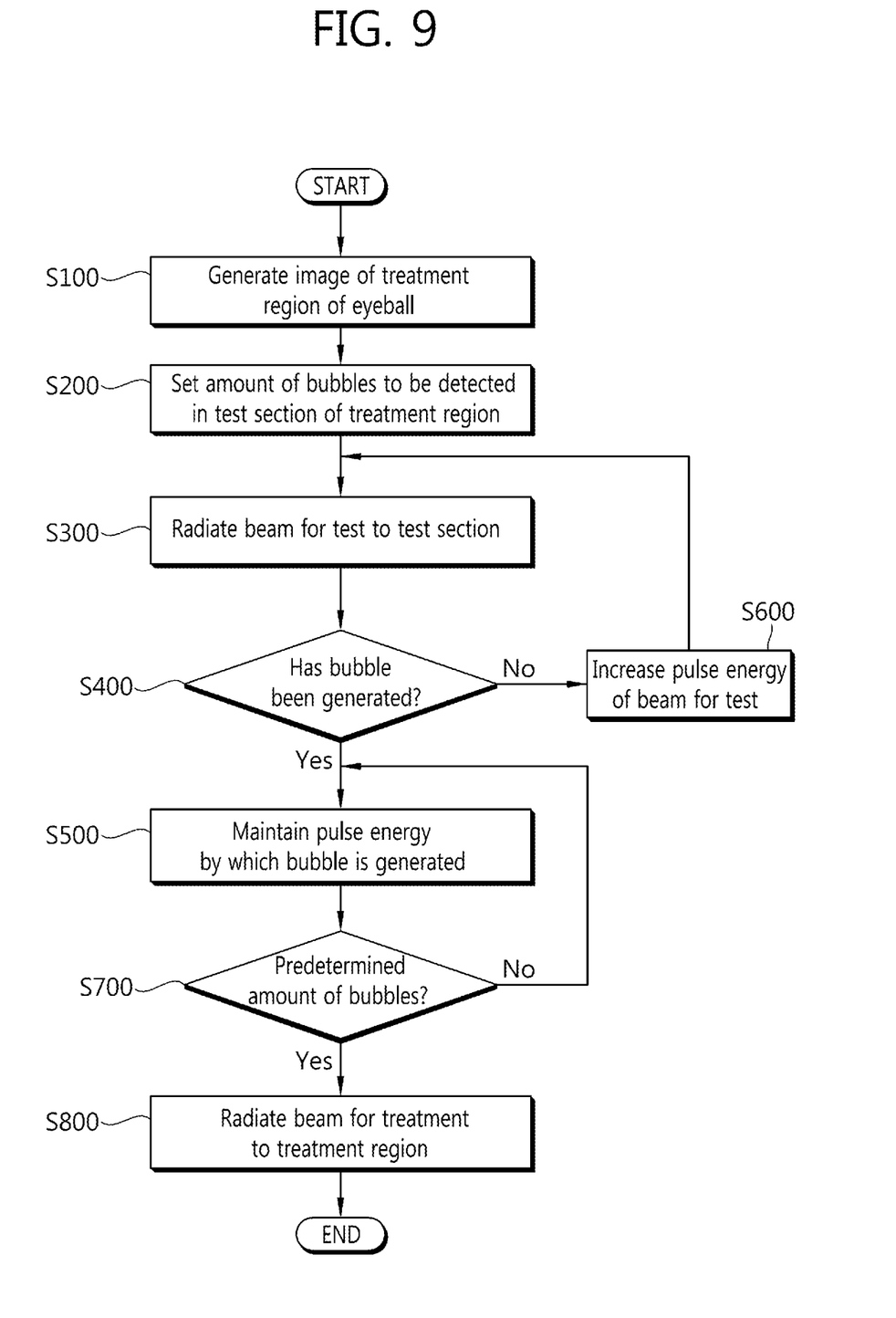
FIG. 9 is a graph illustrating the amounts of energy of beams radiated according to a fourth embodiment.
Figure 10:
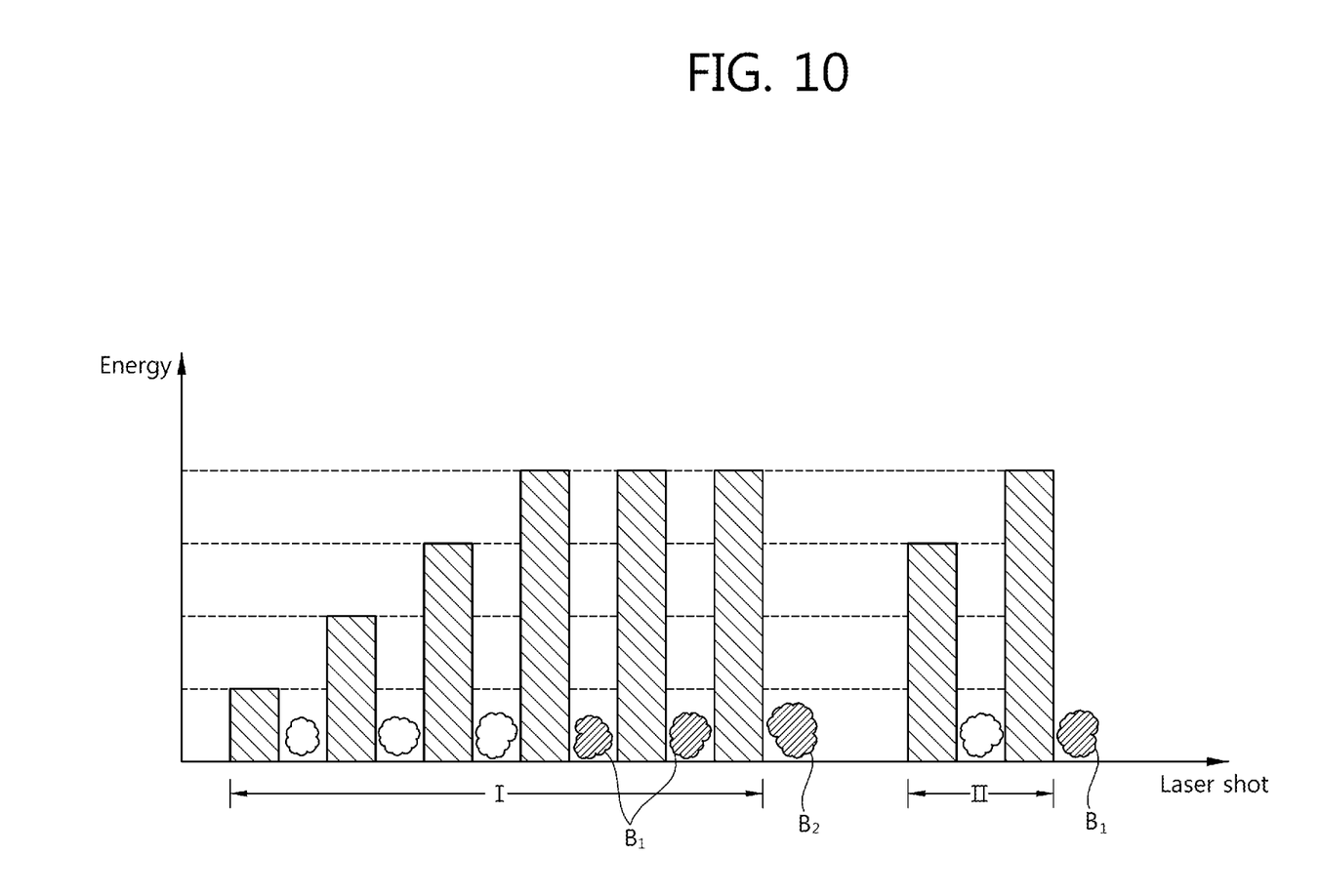
FIG. 10 is a control flowchart illustrating the ophthalmic treatment apparatus in accordance with a fourth embodiment of the present invention.

FIG. 9 is a graph illustrating the amounts of energy of beams radiated according to a fourth embodiment, and FIG. 10 is a control flowchart illustrating the ophthalmic treatment apparatus in accordance with a fourth embodiment of the present invention.

Whether treatment at a treatment location has been completed is determined based on whether a bubble has been generated in the previous embodiments. In contrast, in the present embodiment, treatment may be determined to have been performed if a predetermined amount of bubbles has occurred at a treatment location.

A method of controlling, by the ophthalmic treatment apparatus 1, beams in accordance with the fourth embodiment of the present invention is described below.

As illustrated in FIG. 9, test beams are radiated to a test region I, that is, one region of the treatment region T of the eyeball O. In this case, pulse energy lower than expected pulse energy is used as pulse energy of the beam for test radiated to the test region I. The test beam is radiated to the test region I while sequentially increasing the pulse energy of the beam for test. In this case, the pulse energy of the beam for tests that are sequentially increased preferably is increased at equal intervals. The pulse energy of the beam for test continues to be increased until a bubble B1 is generated.

If the generation of the bubble B1 is detected as test beams are radiated, pulse energy of a beam for test when the bubble B1 is generated is stored in the memory unit 70. Furthermore, a beam for test having the pulse energy until the bubble B1 is generated continues to be radiated until a predetermined amount of bubbles B2 is detected. When the predetermined amount of the bubbles B2 is detected, the time taken to radiate the beam for tests is stored in the memory unit 70. Furthermore, a beam for treatment having the same pulse energy is radiated to the treatment region T based on the information about the pulse energy and the information about the time that are stored in the memory unit 70.

Meanwhile, when a beam for test is radiated to a test region II, that is, the other region of the treatment region T of the eyeball O, a beam for test having pulse energy that is one step lower than the pulse energy when the bubble B1 was generated is radiated based on the information about the pulse energy stored in the memory unit 70. In this case, there is an advantage in that a test time can be reduced when a beam for test is radiated to the test region II, that is, the other region, because the information about the pulse energy previously stored in the memory unit 70 is used as described above.

Such a control flow of the ophthalmic treatment apparatus 1 in accordance with the second embodiment of the present invention is described below.

As illustrated in FIG. 10, first, an image is formed by photographing the treatment region T of the eyeball O (S100). The amount of bubbles B2 to be detected in the test section Te of the treatment region T is set (S200). A beam for test is radiated to the test section Te of the treatment region T (S300). After the beam for test is radiated to the test section Te, whether a bubble B1 has been generated is detected (S400).

If the generation of a bubble B1 is determined to have been detected at step 'S400,' the corresponding test beam maintains its pulse energy (S500). Whether the amount of the bubbles B2 set at step 'S200' is detected is determined (S700). Information about pulse energy and radiation time according to the predetermined amount of the bubbles B2 is stored. A beam for treatment is radiated to the treatment region T based on the stored information about the pulse energy and radiation time (S800).

Meanwhile, if the generation of a bubble B1 is not detected at step 'S400,' the pulse energy of the beam for test is sequentially increased (S600). Furthermore, the process proceeds to the control flow from step 'S300'. Furthermore, if the predetermined amount of the bubbles B2 is not detected at step 'S700,' the proceeds to step 'S500' in which pulse energy of a beam for test when a bubble B1 is generated is maintained until the predetermined amount of the bubbles B2 is detected.

Meanwhile, although not illustrated in FIG. 10, when the beam for test is radiated to a test region II, that is, the other region of the treatment region, at step 'S300,' a beam for test having pulse energy one step lower than stored pulse energy is radiated using the information about the pulse energy of the beam for test radiated to the test region I, that is, one region of the treatment region.

Accordingly, information about pulse energy of a beam for treatment that corresponds to tissue of the treatment region of an eyeball can be obtained because a beam for test is radiated before the beam for treatment is radiated to the treatment region, and thus treatment efficiency and safety of the treatment region can be secured.

As described above, although the embodiments of the present invention have been described with reference to the accompanying drawings, those skilled in the art to which the present invention pertains will understand that the present invention may be implemented in other detailed forms without changing the technical spirit or indispensable characteristics of the present invention. Accordingly, it will be understood that the aforementioned embodiments are illustrative and not limitative from all aspects. The scope of the present invention is defined by the appended claims rather than the detailed description, and the present invention should be construed as covering all modifications or variations derived from the meaning and scope of the appended claims and their equivalents.

What is claimed is:

1. An ophthalmic treatment apparatus, comprising:
 a beam generation unit which generates beams comprising a plurality of pulse trains, wherein each pulse train comprises a plurality of pulses of which energy levels are sequentially increasing;
 a detection unit which detects a signal indicating an occurrence of one or more bubbles generated by the pulse train in a treatment location; and
 a control unit which controls an operation of the beam generation unit based on the signal detected from the detection unit,
 wherein the plurality of the pulse trains comprises a first pulse train being radiated to a first treatment location in a treatment region of an eyeball and a second pulse train being radiated to a second treatment location, and
 wherein the control unit controls an energy level of an initial pulse of the second pulse train based on the signal generated by the first pulse train.

2. The ophthalmic treatment apparatus of claim 1, wherein the control unit controls the energy level of the initial pulse of the second pulse train is lower than a maximum energy level of the first pulse train.

3. The ophthalmic treatment apparatus of claim 1, wherein the first pulse train comprises a first plurality of pulses of which energy levels are sequentially increasing from a first minimum level to a first maximum level and the second pulse train comprises a second plurality of pulses of which energy levels are sequentially increasing from a second minimum level to a second maximum level, and
wherein the control unit controls the second minimum level of the second pulse train to be lower than the first maximum level of the first pulse train.

4. The ophthalmic treatment apparatus of claim 3, wherein the control unit controls the second minimum level to be greater than the first minimum level of the first pulse train.

5. The ophthalmic treatment apparatus of claim 1, wherein the signal detected from the detection unit further indicates an amount of the bubbles generated by the pulse train.

6. The ophthalmic treatment apparatus of claim 1, further comprising a memory unit configured to store information of the pulse train when the signal is detected by the detection unit.

7. The ophthalmic treatment apparatus of claim 1, wherein the control unit controls the operation of the beam generation unit to stop radiation of the first pulse train based on the signal detected by the detection unit.

8. A method of controlling beams by an ophthalmic treatment apparatus, wherein the ophthalmic treatment apparatus comprises a beam generation unit generating beams comprising a plurality of pulse trains and each pulse train comprises a plurality of pulses of which energy levels are sequentially increasing, the method comprising:
generating a first pulse train and radiating the first pulse train to a first treatment location in a treatment region of an eyeball;
detecting, by a detection unit, a signal indicating an occurrence of one or more bubbles generated by the first pulse train in the first treatment location; and
generating a second pulse train and radiating the second pulse train to a second treatment location in the treatment region, wherein an energy level of an initial pulse of the second pulse train is controlled by a control unit based on the signal detected by the detection unit.

9. The method of claim 8, wherein the control unit controls the energy level of the initial pulse of the second pulse train to be lower than a maximum energy level of the first pulse train.

10. The method of claim 8, wherein the first pulse train comprises a plurality of pulses of which energy levels are sequentially increasing from a first minimum level to a first maximum level and the second pulse train comprises a second plurality of pulses of which energy levels are sequentially increasing from a second minimum level to a second maximum level, and
wherein the control unit controls the second minimum level of the second pulse train to be lower than the first maximum level of the first pulse train.

11. The method of claim 10, wherein the control unit controls the second minimum level to be greater than the first minimum level of the first pulse train.

12. The method of claim 8, wherein the signal detected by the detection unit further indicates an amount of the bubbles generated by the first pulse train in the first treatment location.

13. The method of claim 8, further comprising storing information about the first pulse train when the signal is detected by the detection unit.

14. The method of claim 8, wherein the control unit controls to stop radiation of the first pulse train to the first treatment location when the signal is detected by the detection unit.

* * * * *